US009868858B2

(12) United States Patent
Atkinson et al.

(10) Patent No.: US 9,868,858 B2
(45) Date of Patent: Jan. 16, 2018

(54) OPTICAL BRIGHTENING AGENTS FOR HIGH QUALITY INK-JET PRINTING

(71) Applicant: ARCHROMA IP GMBH, Reinach (CH)

(72) Inventors: David Atkinson, Arlesheim (CH); Cristina Dominguez, Saint Louis (FR); Andrew Jackson, Muenchenstein (CH)

(73) Assignee: ARCHROMA IP GMBH, Reinach (CH)

( * ) Notice: Subject to any disclaimer, the term of this patent is extended or adjusted under 35 U.S.C. 154(b) by 0 days.

(21) Appl. No.: 14/778,101

(22) PCT Filed: Mar. 21, 2014

(86) PCT No.: PCT/EP2014/000784
§ 371 (c)(1),
(2) Date: Sep. 18, 2015

(87) PCT Pub. No.: WO2014/146798
PCT Pub. Date: Sep. 25, 2014

(65) Prior Publication Data
US 2016/0177098 A1    Jun. 23, 2016

(30) Foreign Application Priority Data
Mar. 21, 2013  (EP) .................................. 13001466

(51) Int. Cl.
| D21H 21/30 | (2006.01) |
| C09B 23/14 | (2006.01) |
| C07D 251/68 | (2006.01) |
| D06P 5/30 | (2006.01) |
| C09K 11/06 | (2006.01) |
| D21H 17/09 | (2006.01) |
| D06L 4/65 | (2017.01) |

(52) U.S. Cl.
CPC .......... *C09B 23/148* (2013.01); *C07D 251/68* (2013.01); *C09K 11/06* (2013.01); *D06L 4/65* (2017.01); *D06P 5/30* (2013.01); *D21H 17/09* (2013.01); *D21H 21/30* (2013.01); *C09K 2211/1059* (2013.01)

(58) Field of Classification Search
CPC ........ C09H 23/14; C09K 11/06; D21K 21/30; D21K 17/09; C07D 251/68; D06L 3/12
USPC ...................................................... 162/158
See application file for complete search history.

(56) References Cited

U.S. PATENT DOCUMENTS

| 4,271,395 A | 6/1981 | Brinkmann et al. |
| 6,919,452 B1 * | 7/2005 | Kimura ................ C07D 251/68 252/301.21 |
| 7,270,771 B2 * | 9/2007 | Cuesta .................... C09K 11/06 252/301.21 |
| 8,696,867 B2 * | 4/2014 | Hunke ................ C07D 251/68 162/158 |
| 8,696,868 B2 * | 4/2014 | Hunke ................ C07D 251/68 162/158 |
| 8,920,605 B2 * | 12/2014 | Hunke ................ C07D 251/00 162/158 |
| 2004/0029055 A1 * | 2/2004 | Fujita ..................... G03C 7/413 430/466 |
| 2004/0111812 A1 * | 6/2004 | Yamaguchi .......... C07D 251/68 8/648 |
| 2005/0124755 A1 * | 6/2005 | Mitchell ............. C08K 5/0041 524/557 |
| 2007/0245503 A1 * | 10/2007 | Jackson ............... C07D 251/68 8/442 |
| 2010/0129553 A1 * | 5/2010 | Jackson .................. B41M 5/52 427/288 |
| 2011/0094694 A1 * | 4/2011 | Hunke ................ C07D 251/54 162/158 |
| 2011/0126996 A1 * | 6/2011 | Hunke ................ C07D 251/54 162/184 |
| 2013/0126117 A1 * | 5/2013 | Hunke .................. D21H 17/07 162/184 |

FOREIGN PATENT DOCUMENTS

| JP | S44-6983 | 3/1969 |
| JP | 62-273266 | 11/1987 |
| JP | 2005509735 A | 4/2005 |
| JP | 2005532441 | 10/2005 |
| JP | 2006506492 | 2/2006 |
| JP | 2011515597 | 5/2011 |
| JP | 2011522972 | 8/2011 |
| JP | 2012509795 A | 4/2012 |
| JP | 2012509796 | 4/2012 |
| RU | 2330870 C2 | 8/2008 |
| RU | 2380364 C2 | 1/2010 |
| WO | 0046336 A1 | 8/2000 |
| WO | 03/044275 | 5/2003 |
| WO | 2004005617 | 1/2004 |
| WO | 2004005617 A1 | 1/2004 |
| WO | 2004046293 | 6/2004 |
| WO | 2009/118248 | 10/2009 |

(Continued)

OTHER PUBLICATIONS

International Search Report and Written Opinion from corresponding PCT/EP2014/000784, dated Jun. 4, 2014.

*Primary Examiner* — Mark Halpern
(74) *Attorney, Agent, or Firm* — McBee Moore Woodward & Vanik IP, LLC

(57) ABSTRACT

The instant invention relates to mixtures of stilbene compounds which provide superior fluorescent whitening effects when applied to the surface of ink-jet papers.

19 Claims, No Drawings

(56) References Cited

FOREIGN PATENT DOCUMENTS

| WO | 2010/060569 A1 | 11/2009 |
| WO | 2009/150182 | 12/2009 |
| WO | 2010060570 A1 | 6/2010 |
| WO | 2012013513 A1 | 2/2012 |

* cited by examiner

OPTICAL BRIGHTENING AGENTS FOR HIGH QUALITY INK-JET PRINTING

CROSS REFERENCE TO RELATED APPLICATIONS

This application is a §371 National Stage Application of PCT/EP2014/000784, filed 21 Mar. 2014, which claims priority to EP 13001466.5, filed 21 Mar. 2013.

BACKGROUND

Field of the Invention

The instant invention relates to novel stilbene compounds or mixtures of stilbene compounds which provide superior fluorescent whitening effects when applied to the surface of papers, such as ink-jet papers.

Description of Related Art

Ink-jet printing has in recent years become a very important means for recording data and images onto a paper sheet. Low costs, easy production of multicolour images and relatively high speed are some of the advantages of this technology. Ink-jet printing does however place great demands on the substrate in order to meet the requirements of short drying time, high print density and sharpness, and reduced colour-to-colour bleed. Furthermore, the substrate should have a high brightness. Plain papers for example are poor at absorbing the water-based anionic dyes or pigments used in ink-jet printing; the ink remains for a considerable time on the surface of the paper which allows diffusion of the ink to take place and leads to low print sharpness. One method of achieving a short drying time while providing high print density and sharpness is to use special silica-coated papers. Such papers however are expensive to produce.

U.S. Pat. No. 6,207,258 provides a partial solution to this problem by disclosing that pigmented ink-jet print quality can be improved by treating the substrate surface with an aqueous sizing medium containing a divalent metal salt. Calcium chloride and magnesium chloride are preferred divalent metal salts. The sizing medium may also contain other conventional paper additives used in treating uncoated paper. Included in conventional paper additives are optical brightening agents which are well known to improve considerably the whiteness of paper and thereby the contrast between the ink-jet print and the background. U.S. Pat. No. 6,207,258 offers no examples of the use of optical brightening agents with the invention.

The advantages of using a divalent metal salt, such as calcium chloride, in substrates intended for pigmented ink-jet printing can only be fully realized when a compatible water-soluble optical brightening agent becomes available. It is well-known however that water-soluble optical brightening agents are prone to precipitation in high calcium concentrations. (See, for example, page 50 in Tracing Technique in Geohydrology by Werner Kass and Horst Behrens, published by Taylor & Francis, 1998.)

WO 2010/060570 discloses that symmetric diaminostilbene optical brightening agents of formula (1) have surprisingly good compatibility with sizing compositions containing a divalent metal salt.

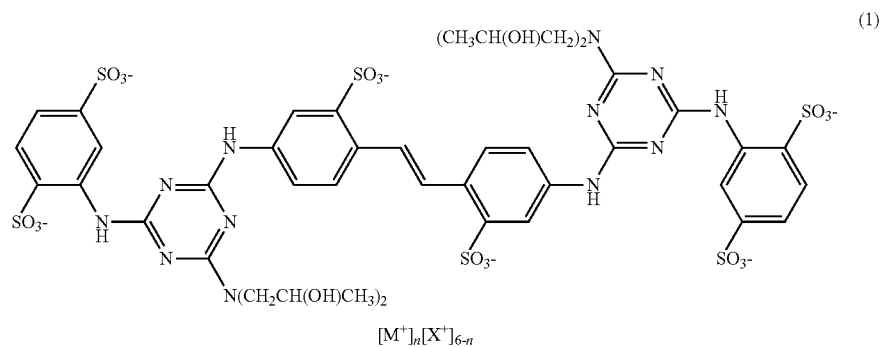

WO 2012/013513 claims an improvement over the prior art by the use of specific stilbene optical brightening agents of which a preferred embodiment (claim 6) has the asymmetric formula (2).

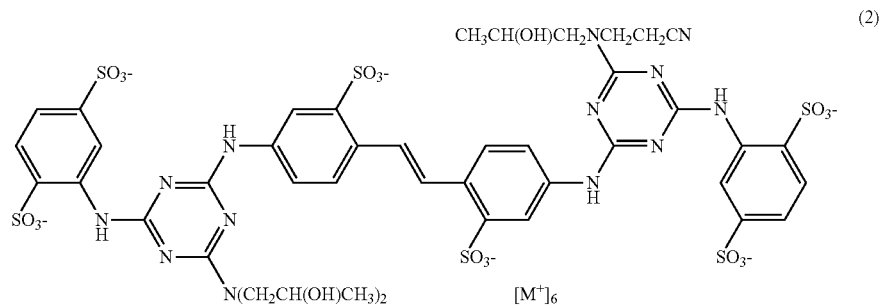

(2)

The demand remains for a water-soluble optical brightening agent which has improved compatibility with sizing compositions containing a divalent metal salt.

SUMMARY

It has now been found that optical brightening agents (OBAs) comprising a stilbene compound of formula (4) and/or a mixture of stilbene compounds of formulae (3), (4) and (5) have surprisingly good compatibility with sizing compositions containing a divalent metal salt and consequently provide superior fluorescent whitening effects when applied to the surface of ink-jet papers.

in which
R is hydrogen or methyl;
Y is a natural or unnatural amino acid from which a hydrogen atom of the amino group has been removed;
and M is hydrogen, an alkali metal cation, ammonium, ammonium which is mono-, di- or trisubstituted by a $C_1$-$C_4$ linear or branched alkyl radical, ammonium which is mono-, di- or trisubstituted by a $C_1$-$C_4$ linear or branched hydroxyalkyl radical, or mixtures of said compounds.

Examples of amino acids from which Y may be derived are alanine, 2-aminobutyric acid, asparagine, aspartic acid, S-carboxymethylcysteine, cysteic acid, cysteine, glutamic acid, glutamine, glycine, iminodiacetic acid, isoleucine,

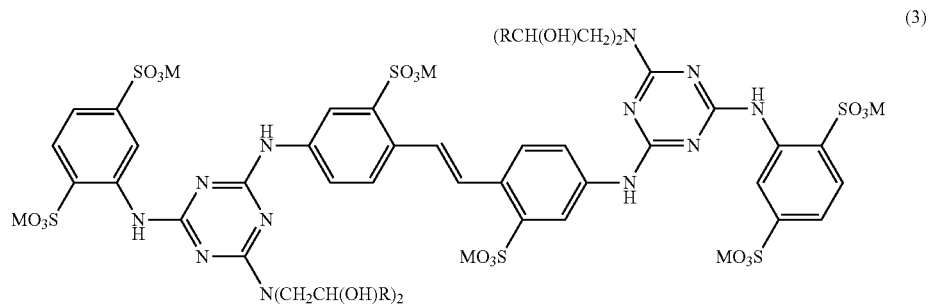

(3)

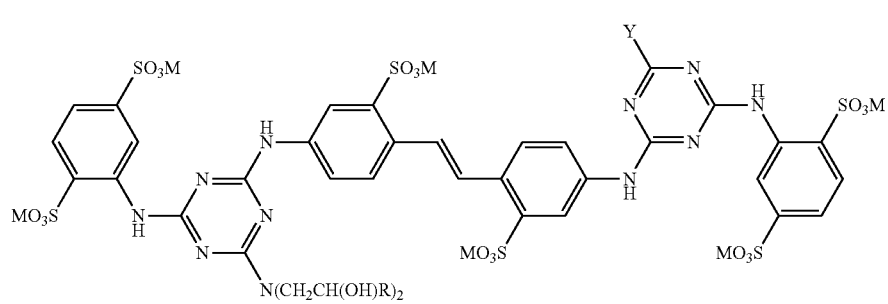

(4)

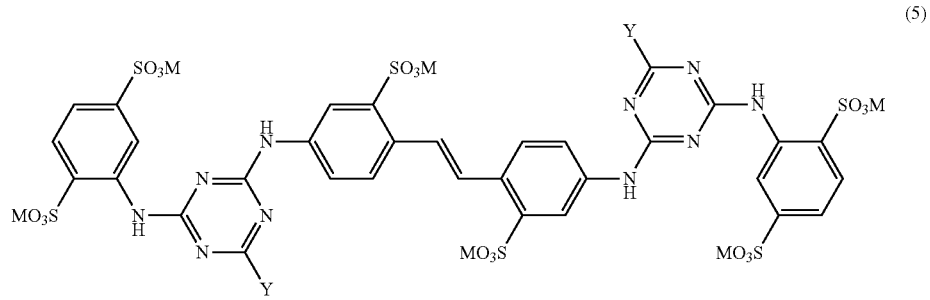

(5)

leucine, methionine, N-methyltaurine, norleucine, norvaline, phenylalanine, 2-phenylglycine, pipecolinic acid, proline, sarcosine, serine, taurine, threonine, and valine. Where the amino acid contains a chiral centre, either optical isomer, or the racemic mixture, can be used.

DETAILED DESCRIPTION OF A PREFERRED EMBODIMENT

In a one aspect of the invention, Y is derived from aspartic acid, glutamic acid or iminodiacetic acid.

In a further aspect of the invention, Y is derived from aspartic acid or iminodiacetic acid, R is methyl and M is sodium.

The mixture of compounds of formulae (3), (4) and (5) may be prepared, for example by the stepwise reaction of a cyanuric halide with a) an amine of formula (6)

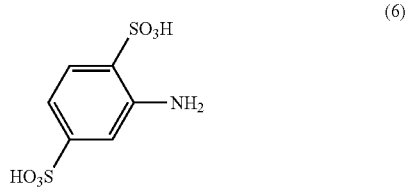 [SMILES: Nc1cc(S(=O)(=O)O)ccc1S(=O)(=O)O]

(6)

in the free acid, partial- or full salt form,
(b) a diamine of formula (7)

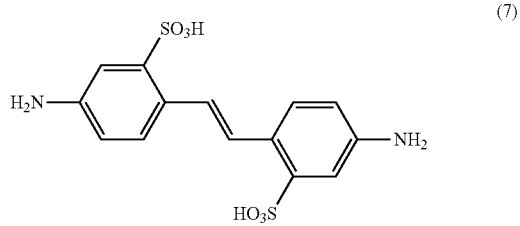 [SMILES: Nc1ccc(/C=C/c2ccc(N)cc2S(=O)(=O)O)c(S(=O)(=O)O)c1]

(7)

in the free acid, partial- or full salt form, and
(c) a mixture of at least one natural or unnatural amino acid, and
(d) at least one of diethanolamine or diisopropanolamine.

As a cyanuric halide there may be employed the fluoride, chloride or bromide. In one embodiment cyanuric chloride is used.

Each reaction may be carried out in an aqueous medium, the cyanuric halide being suspended in water, or in an aqueous/organic medium, the cyanuric halide being dissolved in a solvent such as acetone. Each amine may be introduced without dilution, or in the form of an aqueous solution or suspension. The amines can be reacted in any order, although it is preferred to react the aromatic amines first. Each amine may be reacted stoichiometrically, or in excess. Typically, the aromatic amines are reacted stoichiometrically, or in slight excess; the amine mixture used in the final step is generally employed in an excess of 5-30% over stoichiometry.

For substitution of the first halogen of the cyanuric halide, one may operate at a temperature in the range of 0 to 20° C., and under acidic to neutral pH conditions, e.g. in the pH range of 2 to 7. For substitution of the second halogen of the cyanuric halide, one may operate at a temperature in the range of 20 to 60° C., and under weakly acidic to weakly alkaline conditions, e.g. at a pH in the range of 4 to 8. For substitution of the third halogen of the cyanuric halide, one may operate at a temperature in the range of 60 to 102° C., i.e. up to the boiling point of water under the given reaction conditions, and under weakly acidic to alkaline conditions, e.g. at a pH in the range of 7 to 10.

The pH of each reaction is generally controlled by addition of a suitable base, the choice of base being dictated by the desired product composition. Suitable bases are, for example, alkali metal (e.g., lithium, sodium or potassium) hydroxides, carbonates or bicarbonates, or aliphatic tertiary amines e.g. triethanolamine or triisopropanolamine. Where a combination of two or more different bases is used, the bases may be added in any order, or at the same time.

Where it is necessary to adjust the reaction pH using acid, examples of acids that may be used include hydrochloric acid, sulphuric acid, formic acid and acetic acid.

Aqueous solutions comprising a mixture of compounds (3), (4) and (5) may optionally be desalinated either by membrane filtration or by a sequence of precipitation followed by solution using an appropriate base. Membrane filtration processes that may be used are ultrafiltration using, e.g., polysulphone, polyvinylidene fluoride, cellulose acetate or thin-film membranes.

The proportions of the compounds (3), (4) and (5) may vary considerably depending on both the composition and the mode of addition (sequential or simultaneous) of the mixture of the amino acid and the dialkanolamine. Each of the compounds (3), (4) and (5) may be present in the range of 5-80 mole-%. In one embodiment, compound (3) is present in the range of 5-45 mole-%, compound (4) in the range of 15-65 mole-%, and compound (5) in the range of 5-45 mole-%. In a further embodiment, compound (3) is present in the range of 15-45 mole-%, compound (4) in the range of 25-60 mole-%, and compound (5) in the range of 5-40 mole-%.

Alternatively, compounds of formulae (3), (4) and (5) may be prepared separately and mixed to form the optical brightening agent of the instant invention. Although compounds of formulae (3) and (5) are known compounds and may be prepared by known methods, compounds of formula (4) are new.

Consequently, a further aspect of the invention is a compound of formula (4), an optical brightening agent comprising said compound of formula (4) and optionally further compounds having brightening capabilities. Such further compounds may be selected among the compounds of formula (3) and (5), as respectively defined herein, as well as compounds having brightening capabilities, not explicitly defined herein

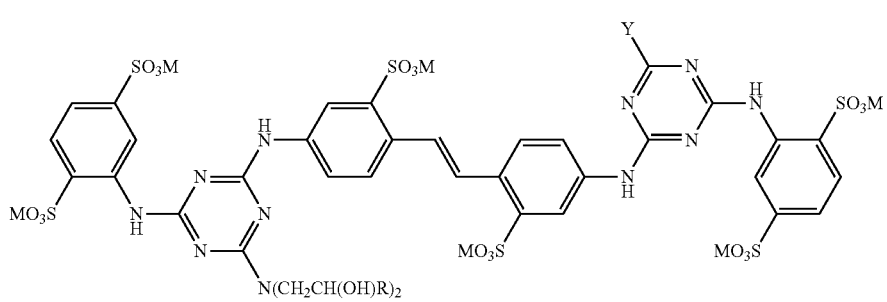

(4)

in which R, Y and M are as previously defined.

A compound of formula (4) may be prepared for example by
i) the stepwise reaction of
  a) a cyanuric halide with an amine of formula (6)

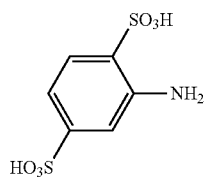

(6)

in the free acid, partial- or full salt form,
(b) an amine of formula (8)

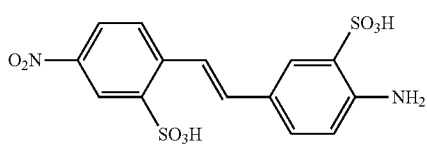

(8)

in the free acid, partial- or full salt form, and
  c) a dialkanolamine (diethanolamine or diisopropanolamine),
ii) reduction of the nitro group to an amino group,
iii) stepwise reaction with
  a) the product of reaction between a cyanuric halide and an amine of formula (6), and
  b) a natural or unnatural amino acid in the free acid, partial- or full salt form.

The invention also relates to the use of a compound of formula (4) in compositions for the surface brightening of paper.

A further aspect of the instant invention is the use of a composition for the surface brightening of paper which comprises a surface sizing agent, an optical brightening agent comprising said compound of formula (4) or a mixture of compounds (3), (4) and (5), a divalent metal salt and water.

The concentration of optical brightening agent in the surface brightening composition may be between 0.2 and 30 g/l, e.g. between 1 and 15 g/l, or between 2 and 12 g/l.

The surface sizing agent is typically an enzymatically or chemically modified starch, e.g. oxidized starch, hydroxyethylated starch or acetylated starch. The starch may also be native starch, anionic starch, a cationic starch, or an amphipathic starch depending on the particular embodiment being practiced. While the starch source may be any, examples of starch sources include corn, wheat, potato, rice, tapioca, and sago.

The concentration of surface sizing agent in the surface brightening composition may be between 1 and 30% by weight, e.g. between 2 and 20% by weight, or between 5 and 15% by weight.

Suitable divalent metal salts are selected from the group consisting of calcium chloride, magnesium chloride, calcium bromide, magnesium bromide, calcium sulphate, magnesium sulphate, calcium thiosulphate or magnesium thiosulphate or mixtures of said compounds.

In a further embodiment, the divalent metal salts are selected from the group consisting of calcium chloride or magnesium chloride or mixtures of said compounds.

The concentration of divalent metal salt in the surface brightening composition may be between 1 and 100 g/l, e.g. between 2 and 75 g/l, or between 5 and 50 g/l.

When the divalent metal salt is a mixture of a calcium salt and a magnesium salt, the amount of calcium salt may be in the range of 0.1 to 99.9%.

The pH value of the surface brightening composition is typically in the range of 5 to 13, e.g. 6 to 11.

In addition to the surface sizing agent, the optical brightening agent, the divalent metal salt and water, the surface brightening composition may comprise by-products formed during the preparation of the optical brightening agent as well as other conventional paper additives. Examples of such additives are carriers, e.g. polyvinyl alcohol, defoamers, wax emulsions, dyes, pigments, monovalent metal salts, e.g. sodium chloride, solubilizing aids, preservatives, complexing agents, cross-linkers, special resins etc.

In a further aspect of the invention, the optical brightening agent may be pre-mixed with polyvinyl alcohol in order to boost the whitening effect in surface brightening compositions. The polyvinyl alcohol may have any hydrolysis level including from 60 to 99%.

The optical brightening agent may comprise any amount of polyvinyl alcohol including from 0.1 to 10% by weight of polyvinyl alcohol.

The surface brightening composition may be applied to the surface of a paper substrate by any surface treatment method known in the art. Examples of application methods include size-press applications, calendar-size applications, tub-sizing, coating applications and spraying applications (see, for example, pages 283-286 in Handbook for Pulp & Paper Technologists by G. A. Smook, 2$^{nd}$ Edition Angus Wilde Publications, 1992 and US 2007/0277950.) The preferred method of application is at the size-press such as puddle size-press or rod-metered size-press. A preformed sheet of paper is passed through a two-roll nip which is flooded with the sizing composition. The paper absorbs some of the composition, the remainder being removed in the nip.

The paper substrate contains a web of cellulose fibres which may be synthetic or sourced from any fibrous plant including woody and non-woody sources. Preferably the cellulose fibres are sourced from hardwood and/or softwood. The fibres may be either virgin fibres or recycled fibres, or any combination of virgin and recycled fibres.

The cellulose fibres contained in the paper substrate may be modified by physical and/or chemical methods as described, for example, in Chapters 13 and 15 respectively in Handbook for Pulp & Paper Technologists by G. A. Smook, $2^{nd}$ Edition Angus Wilde Publications, 1992. One example of a chemical modification of the cellulose fibre is the addition of an optical brightener as described, for example, in EP 884,312, EP 899,373, WO 02/055646, WO 2006/061399, WO 2007/017336, WO 2007/143182, US 2006-0185808, and US 2007-0193707.

The surface brightening composition is prepared by adding the optical brightening agent and the divalent metal salt to a preformed aqueous solution of the surface sizing agent at a temperature of between 20° C. and 90° C. In one embodiment the divalent metal salt is added before the optical brightening agent, and at a temperature of between 50° C. and 70° C.

The paper substrate containing the brightening composition of the present invention may have any ISO brightness, including ISO brightness that is at least 80, at least 90 and at least 95.

The paper substrate containing the brightening composition of the present invention may have any CIE Whiteness, including at least 130, at least 146, at least 150, and at least 156. By using the brightening compositions of the subject application it will be possible to prepare very high white paper of a CIE Whiteness of e.g. 170 or 175 and even higher. The brightening composition has a tendency to enhance the CIE Whiteness of a sheet as compared to conventional surface brightening compositions containing similar levels of optical brightening agents.

The brightening composition of the present invention has a decreased tendency to green a sheet to which it has been applied as compared to that of conventional surface brightening compositions containing comparable amounts of optical brightening agents. Greening is a phenomenon related to saturation of the sheet such that a sheet does not increase in whiteness even as the amount of optical brightening agent is increased. The tendency to green is measured is indicated by the a*-b* diagram, a* and b* being the colour coordinates in the CIE Lab system. Accordingly, the brightening composition of the present invention affords the papermaker the ability to reach higher CIE Whiteness and ISO Brightness in the presence of divalent metal salts.

While the paper substrates of the present invention show enhanced properties suitable for ink-jet printing, the substrates may also be used for multi-purpose and laser-jet printing as well. These applications may include those requiring cut-size paper substrates, as well as paper roll substrates.

The paper substrate of the present invention may contain an image. The image may be formed on the substrate with any substance including dye, pigment and toner.

Once the image is formed on the substrate, the print density may be any optical print density including an optical print density that is at least 1.0, at least 1.2, at least 1.4, at least 1.6. [Methods of measuring optical print density can be found in EP 1775141.

EXAMPLES

The following examples shall demonstrate the instant invention in more details. If not indicated otherwise, "parts" means "parts by weight" and "%" means "% by weight". "$E^1_1$" means the absorbance of a 1% solution measured at the absorption maximum of about 350 nm in a 1 cm spectrophotometric cell.

Preparative Example 1

Stage 1: 50.6 parts aniline-2,5-disulphonic acid are added to 90 parts water and dissolved with the aid of an approx. 30% sodium hydroxide solution at approx. 25° C. and a pH value of approx. 8-9. The obtained solution is added over a period of approx. 50 minutes to 36.9 parts cyanuric chloride dispersed in 54 parts water, 65 parts ice and 0.1 parts of a wetting agent. The temperature is kept below 5° C. using an ice/water bath and if necessary by adding ice into the reaction mixture. The pH is maintained at approx. 4-5 using an approx. 30% sodium hydroxide solution. Stirring is continued at approx. 0-5° C. until completion of the reaction (3-4 hours).

Stage 2: 37.0 parts 4,4'-diaminostilbene-2,2'-disulphonic acid are added over a period of approx. 30 minutes. The pH is maintained at approx. 8-9 with the aid of an approx. 30% sodium hydroxide solution. The resulting mixture is heated at approx. 50-60° C. until completion of the reaction (2-3 hours).

Stage 3: 15.3 parts diisopropanolamine and 15.3 parts L-aspartic acid are then added and the temperature is gradually raised to approx. 100° C. and maintained at 95-100° C. until completion of the reaction (4 hours) while keeping the pH at approx. 8-9 using an approx. 30% sodium hydroxide solution. The temperature is then lowered to 25° C. and the reaction mixture is filtered. The solution is adjusted to strength to give 920 parts of an aqueous solution of $E^1_1$ 61.4 containing 42 parts of a compound of formula (9), 73 parts of a compound of formula (10) and 21 parts of a compound of formula (11).

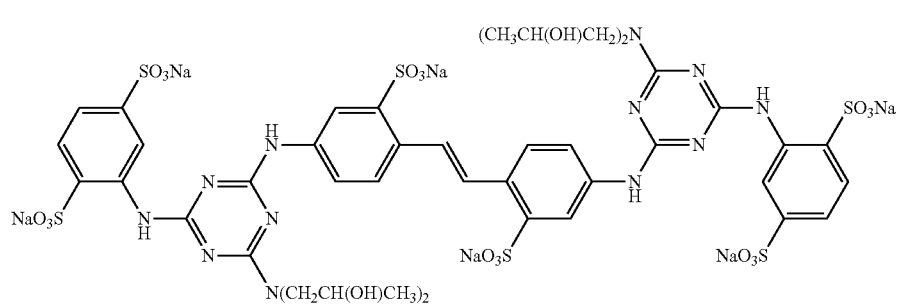

(9)

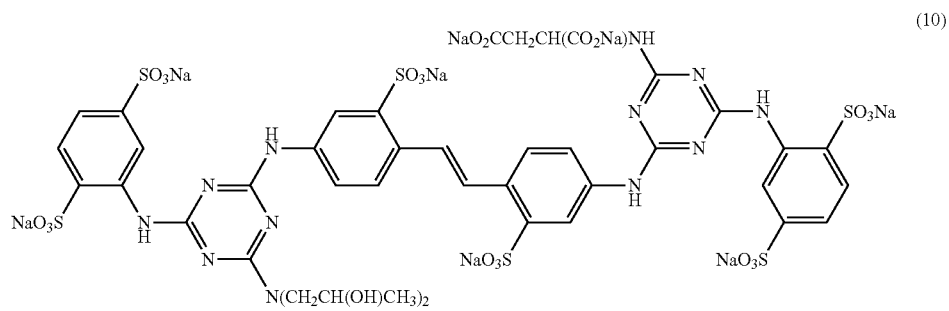

(10)

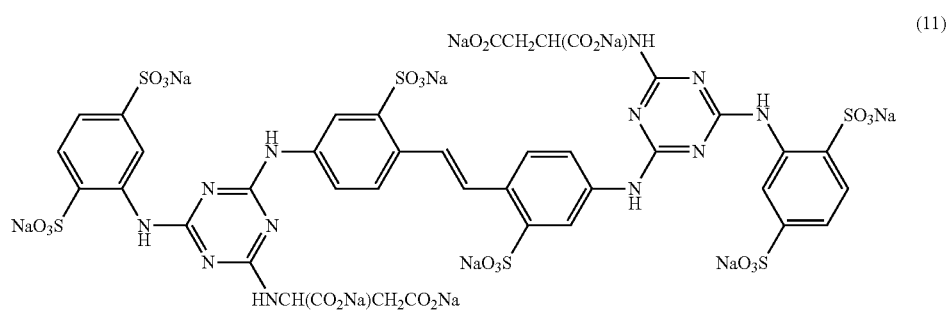

(11)

Compounds (9), (10) and (11) are in proportions of 31 mole-%, 52 mole-% and 14 mole-% respectively.

Preparative Example 2 (Comparative)

As WO 2012/013513 does not disclose a preparative method for the 3-[(2-hydroxypropyl)amino]propionitrile required to make the preferred composition of claim 6 therein, the method given in Example 1 of GB 1,313,469 is followed.

Preparative Example 1 is followed until Stage 2 is completed. 3-[(2-hydroxypropyl)amino]propionitrile, prepared from 8.6 parts isopropanolamine and 6.1 parts acrylonitrile, and 15.3 parts of diisopropanolamine are then added. The temperature is gradually raised to approx. 95° C. and maintained at 95-98° C. until completion of the reaction (4 hours) while keeping the pH at approx. 8-9 using an approx. 30% sodium hydroxide solution. The temperature is then lowered to 50° C. and the reaction mixture is filtered. The solution is adjusted to strength to give 920 parts of an aqueous solution of $E^1_1$ 61.4 containing 31 parts of a compound of formula (9), 38 parts of a compound of formula (12), 23 parts of a compound of formula (13), 14 parts of a compound of formula (14), 15 parts of a compound of formula (15) and 4 parts of a compound of formula (16).

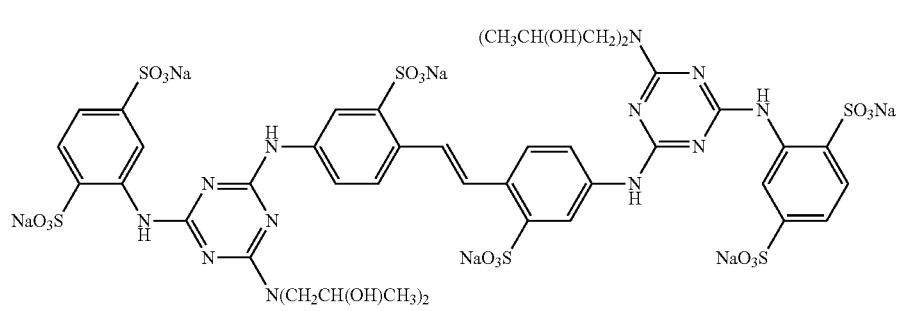
(9)
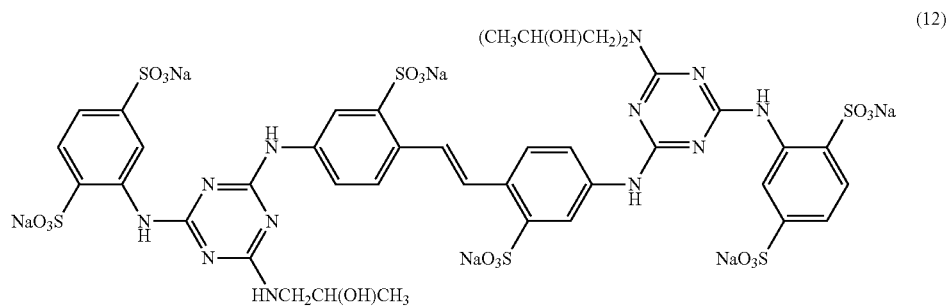
(12)
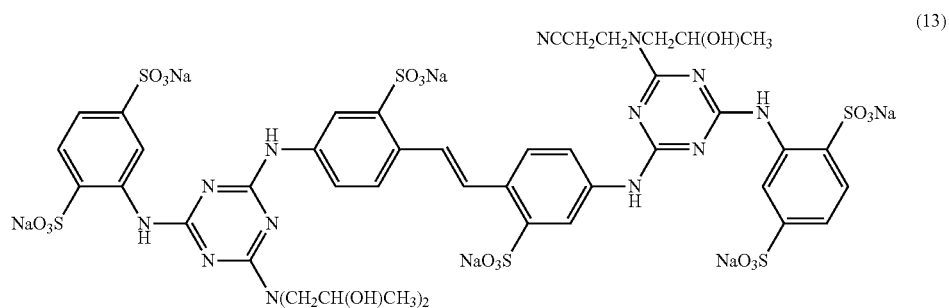
(13)
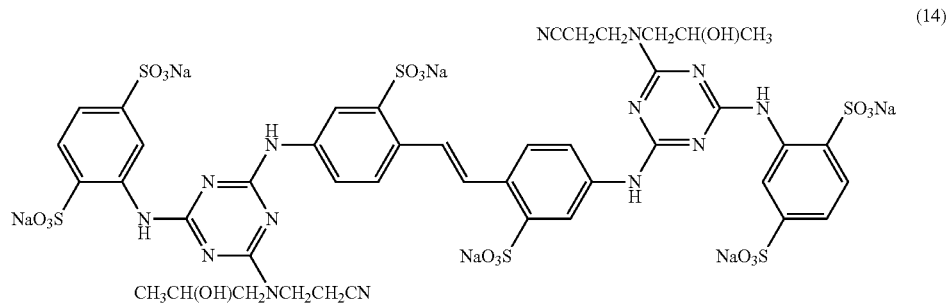
(14)
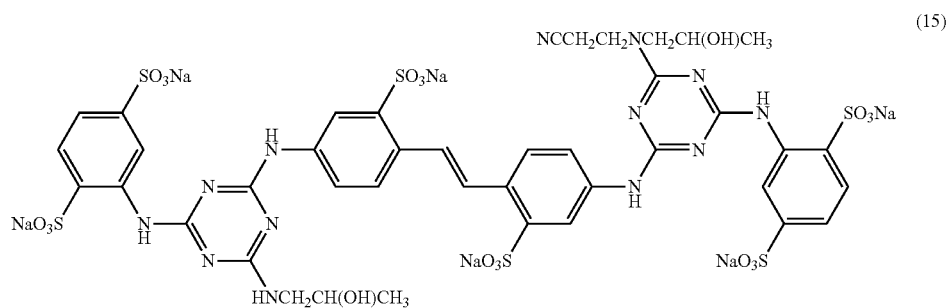
(15)

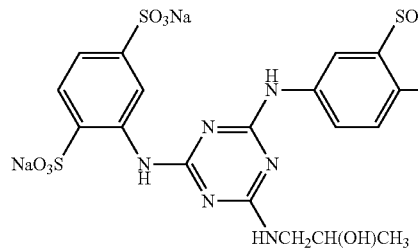
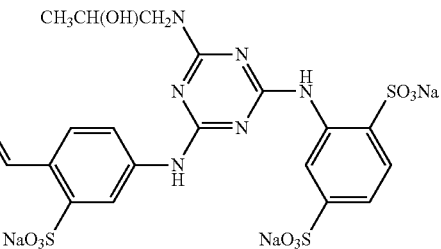

(16)

Compounds (9), (12), (13), (14), (15) and (16) are in proportions of 24 mole-%, 31 mole-%, 18 mole-%, 11 mole-%, 12 mole-% and 3 mole-% respectively.

Preparative Example 3

Preparative Example 1 is followed until Stage 2 is completed. 12.2 parts diisopropanolamine and 18.4 parts L-aspartic acid are then added and the temperature is gradually raised to approx. 100° C. and maintained at 95-100° C. until completion of the reaction (4 hours) while keeping the pH at approx. 8-9 using an approx. 30% sodium hydroxide solution. The temperature is then lowered to 25° C. and the reaction mixture is filtered. The solution is adjusted to strength to give 722 parts of an aqueous solution of $E^1_1$ 76.6 containing 29 parts of a compound of formula (9), 69 parts of a compound of formula (10) and 39 parts of a compound of formula (11). Compounds (9), (10) and (11) are in proportions of 22 mole-%, 51 mole-% and 27 mole-% respectively.

Preparative Example 4

Preparative Example 1 is followed until Stage 2 is completed. 9.2 parts diisopropanolamine and 21.4 parts L-aspartic acid are then added and the temperature is gradually raised to approx. 100° C. and maintained at 95-100° C. until completion of the reaction (4 hours) while keeping the pH at approx. 8-9 using an approx. 30% sodium hydroxide solution. The temperature is then lowered to 25° C. and the reaction mixture is filtered. The solution is adjusted to strength to give 665 parts of an aqueous solution of $E^1_1$ 84.7 containing 17 parts of a compound of formula (9), 66 parts of a compound of formula (10) and 57 parts of a compound of formula (11). Compounds (9), (10) and (11) are in proportions of 12 mole-%, 48 mole-% and 40 mole-% respectively.

Preparative Example 5

Preparative Example 1 is followed until Stage 2 is completed. 18.4 parts diisopropanolamine and 12.2 parts L-aspartic acid are then added and the temperature is gradually raised to approx. 100° C. and maintained at 95-100° C. until completion of the reaction (4 hours) while keeping the pH at approx. 8-9 using an approx. 30% sodium hydroxide solution. The temperature is then lowered to 25° C. and the reaction mixture is filtered. The solution is adjusted to strength to give 575 parts of an aqueous solution of $E^1_1$ 86.5 containing 52 parts of a compound of formula (9), 54 parts of a compound of formula (10) and 17 parts of a compound of formula (11). Compounds (9), (10) and (11) are in proportions of 43 mole-%, 43 mole-% and 13 mole-% respectively.

Preparative Example 6

Preparative Example 1 is followed until Stage 2 is completed. 21.4 parts diisopropanolamine and 9.2 parts L-aspartic acid are then added and the temperature is gradually raised to approx. 100° C. and maintained at 95-100° C. until completion of the reaction (4 hours) while keeping the pH at approx. 8-9 using an approx. 30% sodium hydroxide solution. The temperature is then lowered to 25° C. and the reaction mixture is filtered. The solution is adjusted to strength to give 615 parts of an aqueous solution of $E^1_1$ 85.9 containing 77 parts of a compound of formula (9), 47 parts of a compound of formula (10) and 56 parts of a compound of formula (11). Compounds (9), (10) and (11) are in proportions of 43 mole-%, 26 mole-% and 30 mole-% respectively.

Preparative Example 7

Preparative Example 1 is followed until Stage 2 is completed. 15.3 parts diisopropanolamine and 15.3 parts sodium iminodiacetate are then added and the temperature is gradually raised to approx. 100° C. and maintained at 95-100° C. until completion of the reaction (4 hours) while keeping the pH at approx. 8-9 using an approx. 30% sodium hydroxide solution. The temperature is then lowered to 25° C. and the reaction mixture is filtered. The solution is adjusted to strength to give 608 parts of an aqueous solution of $E^1_1$ 82.1 containing 29 parts of a compound of formula (9), 46 parts of a compound of formula (17) and 51 parts of a compound of formula (18).

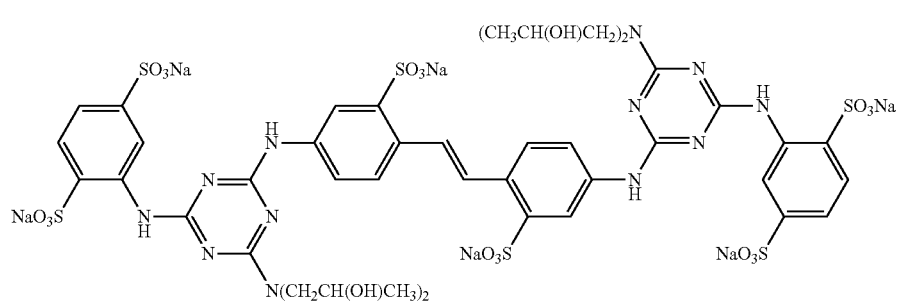

(9)

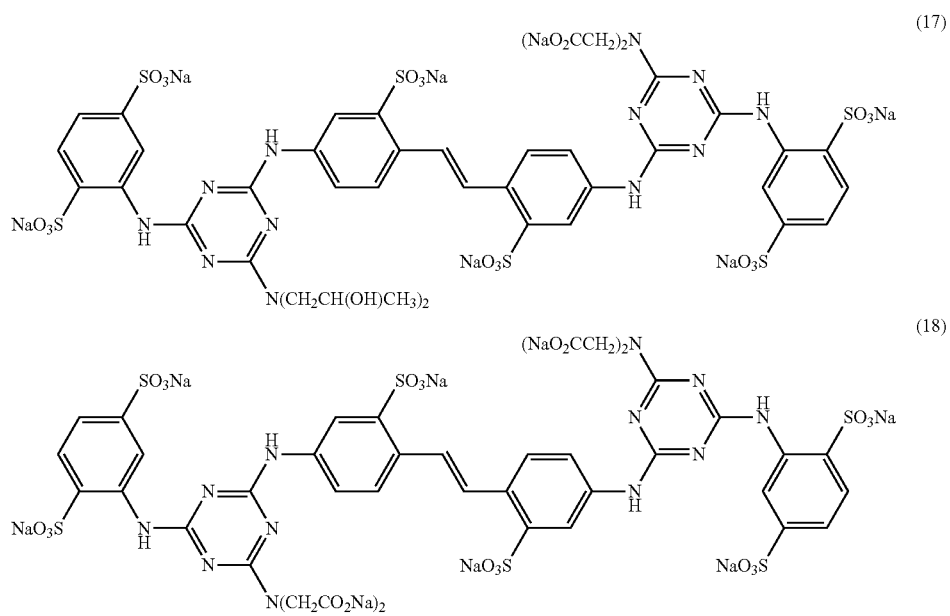

(17)

(18)

Compounds (9), (17) and (18) are in proportions of 24 mole-%, 37 mole-% and 39 mole-% respectively.]

Preparative Example 8

Preparative Example 1 is followed until Stage 2 is completed. 15.3 parts diethanolamine and 15.3 parts L-aspartic acid are then added and the temperature is gradually raised to approx. 100° C. and maintained at 95-100° C. until completion of the reaction (4 hours) while keeping the pH at approx. 8-9 using an approx. 30 sodium hydroxide solution. The temperature is then lowered to 25° C. and the reaction mixture is filtered. The solution is adjusted to strength to give 586 parts of an aqueous solution of $E^1_1$ 84.5 containing 35 parts of a compound of formula (11), 56 parts of a compound of formula (19) and 33 parts of a compound of formula (20).

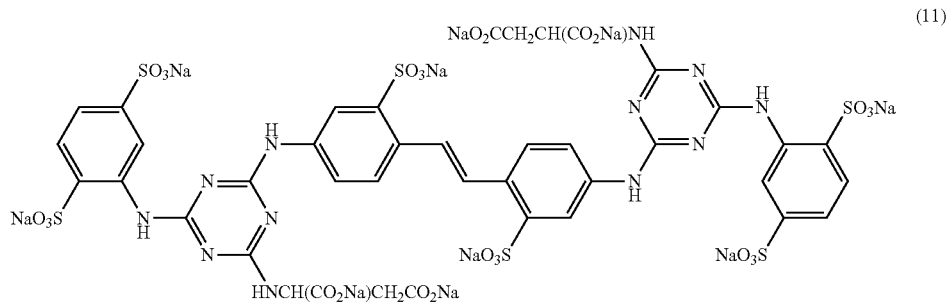

(11)

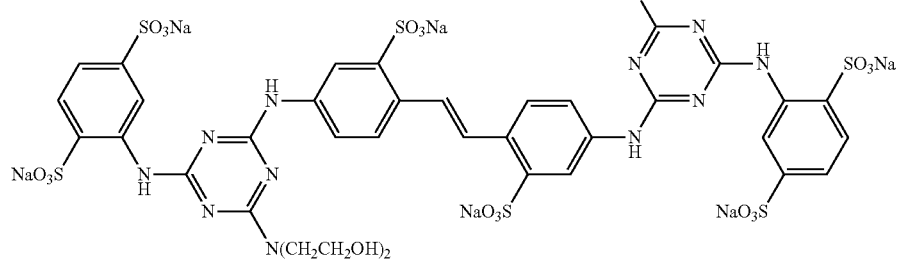

(19)

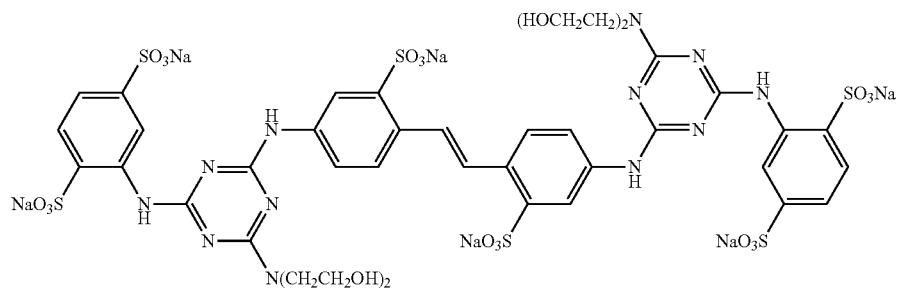

(20)

Compounds (11), (19) and (20) are in proportions of 27 mole-%, 45 mole-% and 28 mole-% respectively.

Preparative Example 9

Preparative Example 1 is followed until Stage 2 is completed. 15.3 parts diisopropanolamine and 16.9 parts L-glutamic acid are then added and the temperature is gradually raised to approx. 100° C. and maintained at 95-100° C. until completion of the reaction (4 hours) while keeping the pH at approx. 8-9 using an approx. 30% sodium hydroxide solution. The temperature is then lowered to 25° C. and the reaction mixture is filtered. The solution is adjusted to strength to give 599 parts of an aqueous solution of $E^1_{\ 1}$ 87.4 containing 28 parts of a compound of formula (9), 67 parts of a compound of formula (21) and 38 parts of a compound of formula (22).

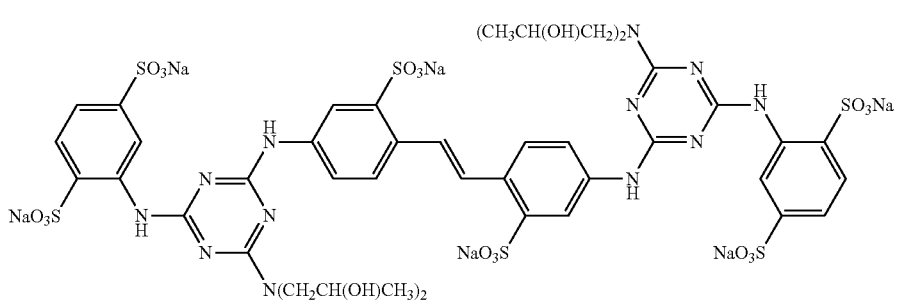

(9)

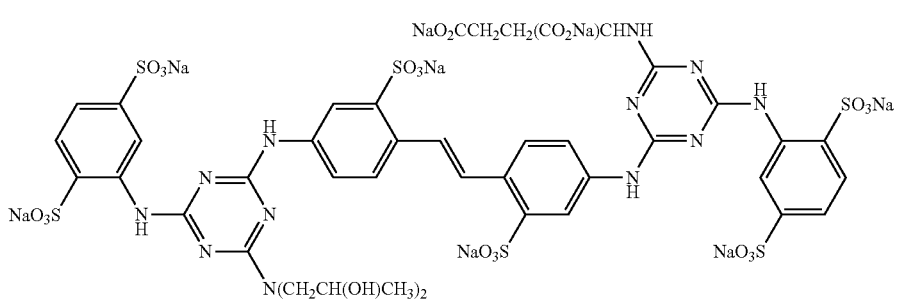

(21)

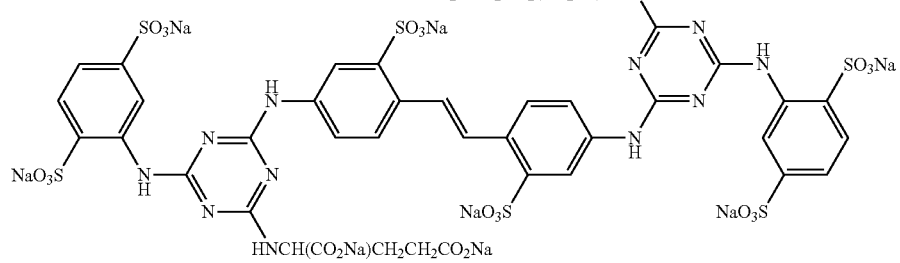

Compounds (9), (21) and (22) are in proportions of 22 mole-%, 50 mole-% and 27 mole-% respectively.

Application Example

Surface brightening compositions are prepared by adding aqueous solutions made according to Preparative Examples 1 and 2 at a range of concentrations from 0 to 40 g/l (from 0 to approx. 8.0 g/l of optical brightening agent) to a stirred, aqueous solution of calcium chloride (35 g/l) and an anionic starch (50 g/l) (Penford Starch 260) at 60° C. The sizing solution is allowed to cool, then poured between the moving rollers of a laboratory size-press and applied to a commercial 75 g/m² AKD (alkyl ketene dimer) sized, bleached paper base sheet. The treated paper is dried for 5 minutes at 70° C. in a flat bed drier.

The dried paper is allowed to condition, and then measured for CIE whiteness on a calibrated Auto Elrepho spectrophotometer. The results are shown in Table 1.

TABLE 1

| Conc. OBA at $E^1_1$ 61.4 [g/l] | Example 1 | | | Example 2 (Comparative) | | |
|---|---|---|---|---|---|---|
| | CIE Whiteness | a* | b* | CIE Whiteness | a* | b* |
| 0 | 100.87 | 1.092 | −2.743 | 100.87 | 1.092 | −2.743 |
| 2.5 | 108.95 | 1.479 | −4.454 | 108.39 | 1.442 | −4.344 |
| 5.0 | 115.43 | 1.757 | −5.847 | 114.31 | 1.727 | −5.599 |
| 10.0 | 123.52 | 2.117 | −7.559 | 120.56 | 1.976 | −6.951 |
| 15.0 | 128.20 | 2.263 | −8.554 | 125.64 | 2.161 | −8.013 |
| 20.0 | 131.01 | 2.329 | −9.147 | 128.41 | 2.213 | −8.613 |
| 30.0 | 133.91 | 2.343 | −9.753 | 131.23 | 2.198 | −9.181 |
| 40.0 | 135.91 | 2.235 | −10.143 | 133.23 | 2.065 | −9.571 |

The results in Table 1 clearly demonstrate the improved whitening effect afforded by the compositions of the invention which additionally provide a more attractive redder (higher a* value) and bluer (more negative b* value) shade.

The invention claimed is:

1. An optical brightening agent comprising a mixture of compounds of formulae (3), (4) and (5)

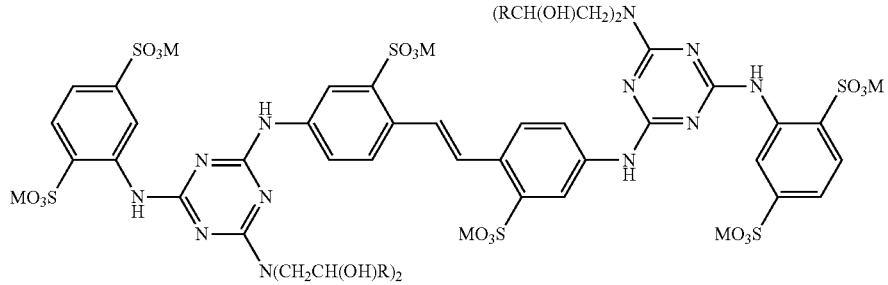

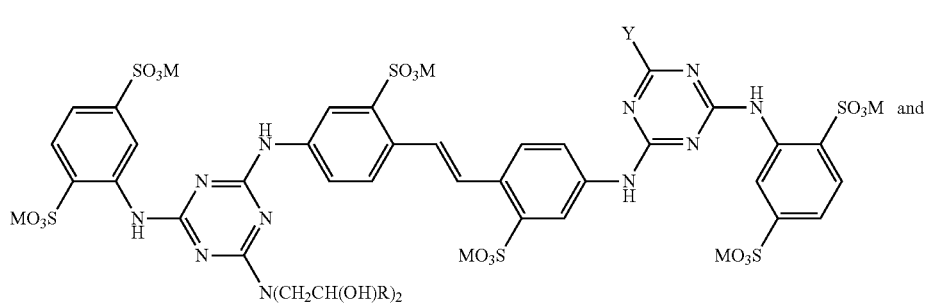

-continued

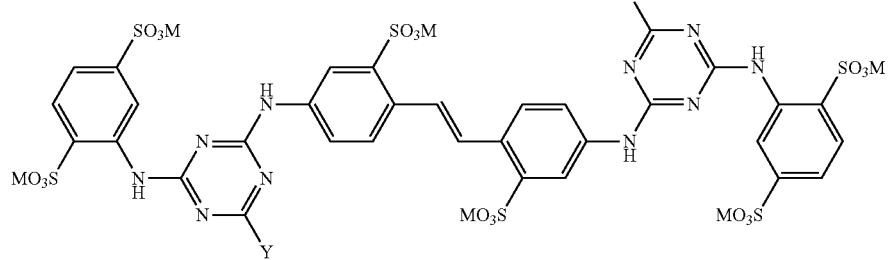

in which

R is hydrogen or methyl;

Y is a natural or unnatural amino acid from which a hydrogen atom of the amino group has been removed; and M is hydrogen, an alkali metal cation, ammonium, ammonium which is mono-, di- or trisubstituted by a $C_1$-$C_4$ linear or branched alkyl radical, ammonium which is mono-, di- or trisubstituted by a $C_1$-$C_4$ linear or branched hydroxyalkyl radical.

2. An optical brightening agent according to claim 1 in which
Y is derived from aspartic acid, glutamic acid or iminodiacetic acid.

3. An optical brightening agent according to claim 1 in which
Y is derived from aspartic acid or iminodiacetic acid,
R is methyl, and
M is sodium.

4. An optical brightening agent according to claim 1, wherein compound (3) is present in the range of 5-45 mole-%, compound (4) is present in the range of 15-65 mole-%, and compound (5) is present in the range of 5-45 mole-%.

5. A process for the preparation of an optical brightening agent comprising compounds of formulae (3), (4) and (5) according to claim 1, wherein cyanuric halide is reacted stepwise with a) an amine of formula (6)

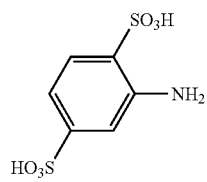

in free acid, partial- or full salt form, (b) a diamine of formula (7)

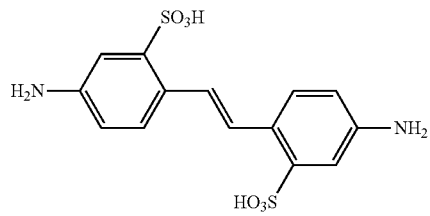

in free acid, partial- or full salt form, and c) a mixture of at least one natural or unnatural amino acid, and d) at least one of diethanolamine or diisopropanolamine.

6. A process according to claim 5, wherein substitution of a first halogen of cyanuric halide is carried out at a temperature in the range from 0 to 20° C. under acidic to neutral pH conditions, and wherein substitution of a second halogen of cyanuric halide is carried out at a temperature in the range from 20 to 60° C. under weakly acidic to weakly alkaline conditions, at a pH in the range from 4 to 8, and wherein substitution of a third halogen of cyanuric halide is carried out at a temperature in the range from 60 to 102° C. under weakly acidic to alkaline conditions, at a pH in the range from 7 to 10.

7. A process according to claim 5, wherein compound (3) is employed in the range of 5-45 mole-%, compound (4) in the range of 15-65 mole-%, and compound (5) in the range of 5-45 mole-%.

8. A composition for surface brightening of paper which comprises a surface sizing agent, an optical brightening agent according to claim 1, a divalent metal salt and water.

9. A surface brightening composition according to claim 8 in which the concentration of optical brightening agent in the surface brightening composition is between 0.2 and 30 g/l.

10. A surface brightening composition according to claim 8 in which the composition additionally comprises polyvinyl alcohol.

11. A surface brightening composition according to claim 8 capable of being used in size-press, calendar-size, tub-size, coating and/or spraying applications.

12. Paper, which has been optically brightened by an optical brightening agent according to claim 1.

13. An optical brightening agent comprising a compound of formula (4)

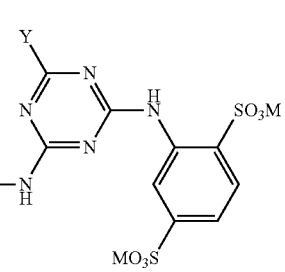

(4)

in which
R is hydrogen or methyl;
Y is derived from aspartic acid, glutamic acid or iminodiacetic acid;
M is hydrogen, an alkali metal cation, ammonium, ammonium which is mono-, di- or trisubstituted by a $C_1$-$C_4$ linear or branched alkyl radical, ammonium which is mono-, di- or trisubstituted by a $C_1$-$C_4$ linear or branched hydroxyalkyl radical,
and optionally one or more further compounds having optical brightening characteristics.

14. The optical brightening agent of claim 13, wherein Y is derived from aspartic acid or iminodiacetic acid.

15. A composition for surface brightening of paper comprises a surface sizing agent, the optical brightening agent of claim 13, a divalent metal salt, and water.

16. The composition of claim 15, wherein the concentration of the optical brightening agent in the composition is between 0.2 and 30 g/l.

17. The composition of claim 15, further comprises polyvinyl alcohol.

18. Paper, which has been optically brightened by the optical brightening agent of claim 13.

19. A compound of formula (4)

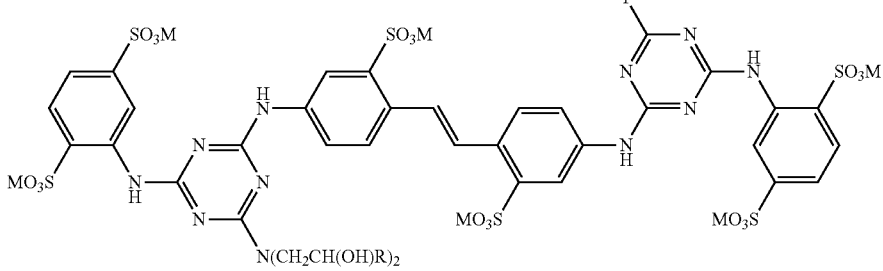

(4)

in which
R is hydrogen or methyl;
Y is derived from aspartic acid, glutamic acid or iminodiacetic acid;
M is hydrogen, an alkali metal cation, ammonium, ammonium which is mono-, di- or trisubstituted by a $C_1$-$C_4$ linear or branched alkyl radical, ammonium which is mono-, di- or trisubstituted by a $C_1$-$C_4$ linear or branched hydroxyalkyl radical.

* * * * *